US009827086B2

(12) United States Patent
Winner et al.

(10) Patent No.: US 9,827,086 B2
(45) Date of Patent: Nov. 28, 2017

(54) TAPERED TUBULAR IMPLANT FORMED FROM WOVEN FABRIC

(71) Applicant: SECANT MEDICAL, INC., Telford, PA (US)

(72) Inventors: Seth A. Winner, Glenside, PA (US); Jack Coy, Wapwallopen, PA (US)

(73) Assignee: The Secant Group, LLC, Telford, PA (US)

(*) Notice: Subject to any disclaimer, the term of this patent is extended or adjusted under 35 U.S.C. 154(b) by 237 days.

(21) Appl. No.: 14/823,240

(22) Filed: Aug. 11, 2015

(65) Prior Publication Data

US 2015/0342721 A1 Dec. 3, 2015

Related U.S. Application Data

(62) Division of application No. 13/752,494, filed on Jan. 29, 2013, now Pat. No. 9,492,268.

(Continued)

(51) Int. Cl.
*A61F 2/06* (2013.01)
*D03D 3/02* (2006.01)
(Continued)

(52) U.S. Cl.
CPC ............... *A61F 2/06* (2013.01); *D02H 13/18* (2013.01); *D03D 3/02* (2013.01); *D03D 3/06* (2013.01);
(Continued)

(58) Field of Classification Search
CPC ........ A61F 2/06; A61F 2/07; A61F 2002/065; A61F 2/04; A61F 2/90; A61F 2250/0039; A61F 2230/0067; A61F 2/88; A61F 2210/0076; A61F 2230/0076; A61F 2250/0017; A61F 2/86; A61F 2230/0054; A61F 2230/006; A61F 2240/001; A61F 2250/0007; A61F 2250/0015; A61F 2250/0026; A61F 2250/0036; D03D 3/02; D03D 3/06; D03D 49/62; D03D 25/005;
(Continued)

(56) References Cited

U.S. PATENT DOCUMENTS

| 180,790 | A | * | 8/1876 | Reed | ......................... | B05B 1/34 |
| | | | | | | 138/123 |
| 5,800,514 | A | * | 9/1998 | Nunez | ...................... | A61F 2/06 |
| | | | | | | 139/384 R |

(Continued)

FOREIGN PATENT DOCUMENTS

WO 2009085281 A1 7/2009

*Primary Examiner* — Bobby Muromoto, Jr.
(74) *Attorney, Agent, or Firm* — McNess Wallace & Nurick LLC

(57) ABSTRACT

A tubular woven implantable graft having a tapered section is provided. The graft includes a first diameter and a second diameter and has a generally constant number of warp yarns per inch adjacent both the first diameter and the second diameter. A method for producing an implantable woven graft is also provided. The method includes weaving a first section having a first diameter and a tapered diameter tapering from the first diameter to a second diameter. During weaving of the tapered section a number of warp yarns are dropped from the weave and compressive forces are applied to the fabric to narrow the width of the fabric.

10 Claims, 8 Drawing Sheets

Related U.S. Application Data

(60) Provisional application No. 61/725,918, filed on Nov. 13, 2012.

(51) Int. Cl.
*D02H 13/18* (2006.01)
*D03D 3/06* (2006.01)
*D03D 49/62* (2006.01)

(52) U.S. Cl.
CPC ...... *D03D 49/62* (2013.01); *A61F 2230/0067* (2013.01); *D10B 2509/06* (2013.01)

(58) Field of Classification Search
CPC ...... D03D 41/004; D03D 49/68; D03D 11/02; D03D 13/008; D03D 15/00
See application file for complete search history.

(56) References Cited

U.S. PATENT DOCUMENTS

| | | | | |
|---|---|---|---|---|
| 6,814,754 B2* | 11/2004 | Greenhalgh | ............. | A61F 2/06 623/1.51 |
| 6,974,586 B2* | 12/2005 | Greenhalgh | ........ | A61B 17/1128 424/423 |
| 6,994,724 B2* | 2/2006 | Schmitt | .................... | A61F 2/04 139/387 R |
| 9,492,268 B2* | 11/2016 | Winner | .................... | D03D 3/02 |
| 2002/0058991 A1* | 5/2002 | Schmitt | .................... | A61F 2/04 623/1.15 |
| 2003/0196717 A1* | 10/2003 | Nunez | ...................... | A61F 2/06 139/1 R |
| 2005/0131516 A1* | 6/2005 | Greenhalgh | ............. | A61F 2/07 623/1.13 |
| 2009/0282908 A1* | 11/2009 | Homayoun | .......... | D03D 1/0088 73/159 |
| 2012/0165918 A1* | 6/2012 | Du | ............................ | A61F 2/06 623/1.15 |
| 2014/0135906 A1* | 5/2014 | Winner | .................... | D03D 3/02 623/1.51 |
| 2015/0320542 A1* | 11/2015 | Gabriele | ................ | A61L 31/06 623/1.13 |
| 2016/0270897 A1* | 9/2016 | Whiting | .................... | A61F 2/04 |
| 2016/0305050 A1* | 10/2016 | Winner | ................ | D03D 41/004 |

* cited by examiner

TAPERED TUBULAR IMPLANT FORMED FROM WOVEN FABRIC

RELATED APPLICATION

The present application claims priority to, and is a division of, U.S. application Ser. No. 13/752,494, filed Jan. 29, 2013 which claims priority U.S. Provisional Patent Application No. 61/725,918 filed Nov. 13, 2012. The entire description of the foregoing applications are hereby incorporated herein by reference.

FIELD OF THE INVENTION

The present invention relates to the field of woven implants. In particular the present invention relates to tubular woven materials that are used to create prosthesis to be implanted into patients. The implants have particular application to the field of vascular implants.

BACKGROUND

Woven fabrics may be used during surgery to repair or replace various damaged or diseased lumens within the human body. A typical surgical procedure is vascular surgery in which a woven tubular prosthesis is used to repair a blood vessel. Grafts in which the lumen has a constant diameter have been used successfully, however, problems have persisted in procedures in which the lumen diameter changes. In one application, the lumen tapers from a first diameter to a smaller second diameter. In another application, the lumen branches. In a branched application, the implant may be formed by suturing together a number of separate lumens. Such a procedure is time consuming. Other known procedures of weaving bifurcated implants result in unacceptable seams and/or transitions.

Additionally, it is desirable to maintain a substantially consistent porosity in a woven implant. In particular, changes in porosity can lead to unacceptable voids or gaps in an implant that would require suturing during the procedure to eliminate potential leakage through the wall of the implant.

SUMMARY OF THE INVENTION

In light of the foregoing, the present invention provides a method and apparatus for forming a woven tubular implant having one or more tapered or bifurcated sections. According to one aspect, the present invention provides a method for forming an implantable graft. The method comprises the steps of weaving a plurality of warp yarns including base yarns and supplemental yarns. The textile includes a tapered section in which the width of the textile changes from a first width to a second width. During the process of weaving the tapered section, a plurality of supplemental yarns are dropped from the weaving process so that the number of ends per inch in the woven section adjacent the first width is similar to the number of ends per inch in the woven section adjacent the second width. Additionally, during the weaving process, compressive forces are applied to the width of the textile. After weaving the fabric, the dropped yarns protrude from the surface of the fabric. Accordingly, the protruding portions of the dropped yarns are trimmed from the fabric.

The present invention also provides an implantable woven graft that includes a first tubular section and a frustoconically shaped hollow tapered section. The first section comprises a woven fabric formed from a plurality of base yarns and a plurality of supplemental yarns. The tapered section has a first diameter that is similar to the first diameter of the first tubular section. The tapered section is woven from the base yarns forming the first tubular section and a plurality of the supplemental yarns. However, the supplemental yarns are dropped from the weave pattern in the tapered section so that ends of the supplemental yarns protrude from the surface of the tapered section. The protruding yarns are spaced apart from one another around the circumference of the tapered section and the number of warp yarns per inch at the second diameter is similar to the number of warp yarns per inch at the first diameter.

DESCRIPTION OF THE DRAWINGS

The foregoing summary and the following detailed description of the preferred embodiments of the present invention will be best understood when read in conjunction with the appended drawings, in which:

FIG. 6A is a view of the loom with a reed in a lowered position;

FIG. 6B is a view of the loom with the reed raised from the position in FIG. 6A;

FIG. 6C is a view of the loom with the reed raised from the position in FIG. 6B;

FIG. 6D is a view of the loom with the reed raised from the position in FIG. 6C;

DETAILED DESCRIPTION OF THE INVENTION

Figure 1:
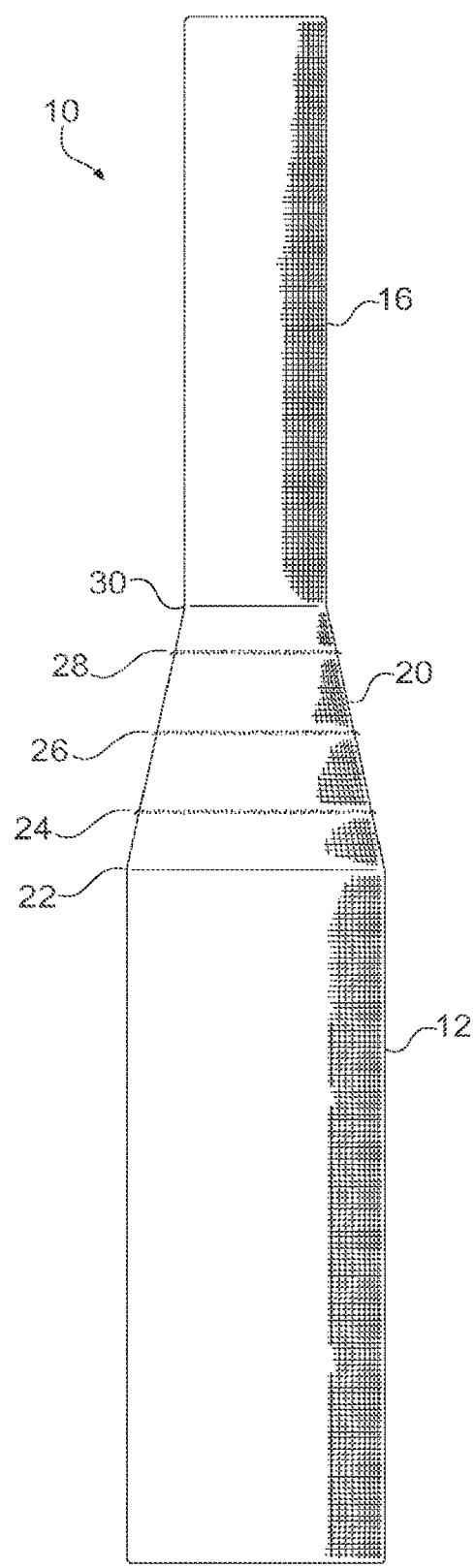
FIG. 1 is a side view of a tapered tubular graft.

Referring now to the drawings in general and to FIG. 1 specifically, a woven graft is designated generally 10. The graft 10 is a woven tubular fabric designed to be implanted into a mammalian body. In particular, the graft is designed to be implanted into a human patient. The graft 10 includes a tapered section 20 in which the graft tapers from a first diameter to a second diameter. Specifically, in the present instance, the graft includes a first portion 12 having a first diameter and a second portion 16 having a second diameter that is smaller than the first diameter. A tapered section 20 has a major diameter corresponding to the first diameter and a minor diameter corresponding to the second diameter so that the tapered section connects the first section 12 with the second section 16 to provide a continuously woven tubular element.

As discussed further below, the graft 10 is formed so that the fabric has substantially similar characteristics along the length of the graft. Specifically, the ends per inch of the warp yarns in the graft is substantially similar in each section 12, 16, 20 of the graft. In this way, features such as the porosity and flexibility of the graft, are substantially similar along the length of the graft.

The graft may be formed from any of a number of natural or synthetic fibers. More than one type of yarn may be used as warp yarns and the fill yarns may differ from the warp yarns. Additionally, more than one type of fill yarn may be used. However, in the present instance, the same material is used for all of the warp yarns and all of the fill yarns. The yarn may be monofilament or multi-filament. In the present instance, the fibers are polyester fibers, such as 1/40/27/12Z PET multi-filament fibers.

The graft 10 is a seamless lumen formed as a flat woven tubular textile. The weave may be any of a variety of weaves, including, but not limited to plain, basket and twill weaves. In the present instance, the graft 10 is formed of a plain double cloth weave forming a flattened tubular structure. The characteristics of the weave pattern may vary depending upon the application for the graft 10. However, in the present instance, the graft 10 is formed so that the walls are substantially impermeable to fluid, so that the graft forms a lumen that is substantially fluid-tight along its length with an inlet 13 and an outlet 17. For example, when used in a vascular application, the walls of the graft are substantially impermeable to blood so that the graft forms a conduit permitting the flow of blood along the axis 15 of the graft while impeding blood leakage through the sidewalls of the graft.

To provide a fluid-tight textile, the fabric comprises approximately 150-350 ends per inch ("EPI") at approximately 100-200 picks per inch ("PPI") for each face. Since the flat woven tube comprises two faces, the total EPI for the graft is approximately 300-700 EPI at approximately 200-400 PPI. More specifically, the fabric may comprise approximately 200-300 EPI at 125-175 PPI for each face. In the present instance, the fabric comprises approximately 225-275 EPI at approximately 150 PPI for each face.

Referring to FIG. 1, the graft 10 comprises two hollow generally cylindrical portions 12, 16 having different diameters and a tapered portion 20 connecting the two cylindrical portions. The tapered portion 20 is a generally frustoconical hollow portion that tapers from the major diameter of the first portion 12 to the minor diameter of the second portion 16. The length of the taper may vary depending on the application. Specifically, the ratio of the length of the tapered portion 20 to the change in diameter from the major diameter to the minor diameter may vary depending on the application.

Although the first portion 12 may taper, in the present instance the first portion is substantially cylindrical having a generally or substantially constant diameter along the length of the first portion. Transition 22 marks the beginning of the taper for the tapered section 20. As discussed further below, during the process of weaving the graft 10, a plurality of warp yarns are dropped from the fabric to reduce the number of ends in the reduced diameter portions of the graft. Depending on the geometry of the tapered section, the dropped yarns may be dropped all at once or the yarns may be dropped in two or more groupings. For instance, in the present instance, the total number of dropped yarns is split among three groups and the groups are dropped at different points of the weaving process.

The point along the length of the graft where the first group of warps yarns is dropped is designated 24 in FIG. 1. As the graft continues to taper inwardly, the point along the length of the graft where the second group of warp yarns is dropped is designated 26. Finally, after the graft tapers further, the point along the length of the graft where the third group of warp yarns is dropped is designated 28. The transition point where the taper of the tapered section 20 discontinues is designated 30. Similar to the first section 12, the second section 16 of the graft may taper along its length at a taper different than the taper of the tapered section. However, in the present instance, the second section 16 is generally or substantially cylindrical so that the diameter of the second section remains substantially constant along its length.

Figure 4:
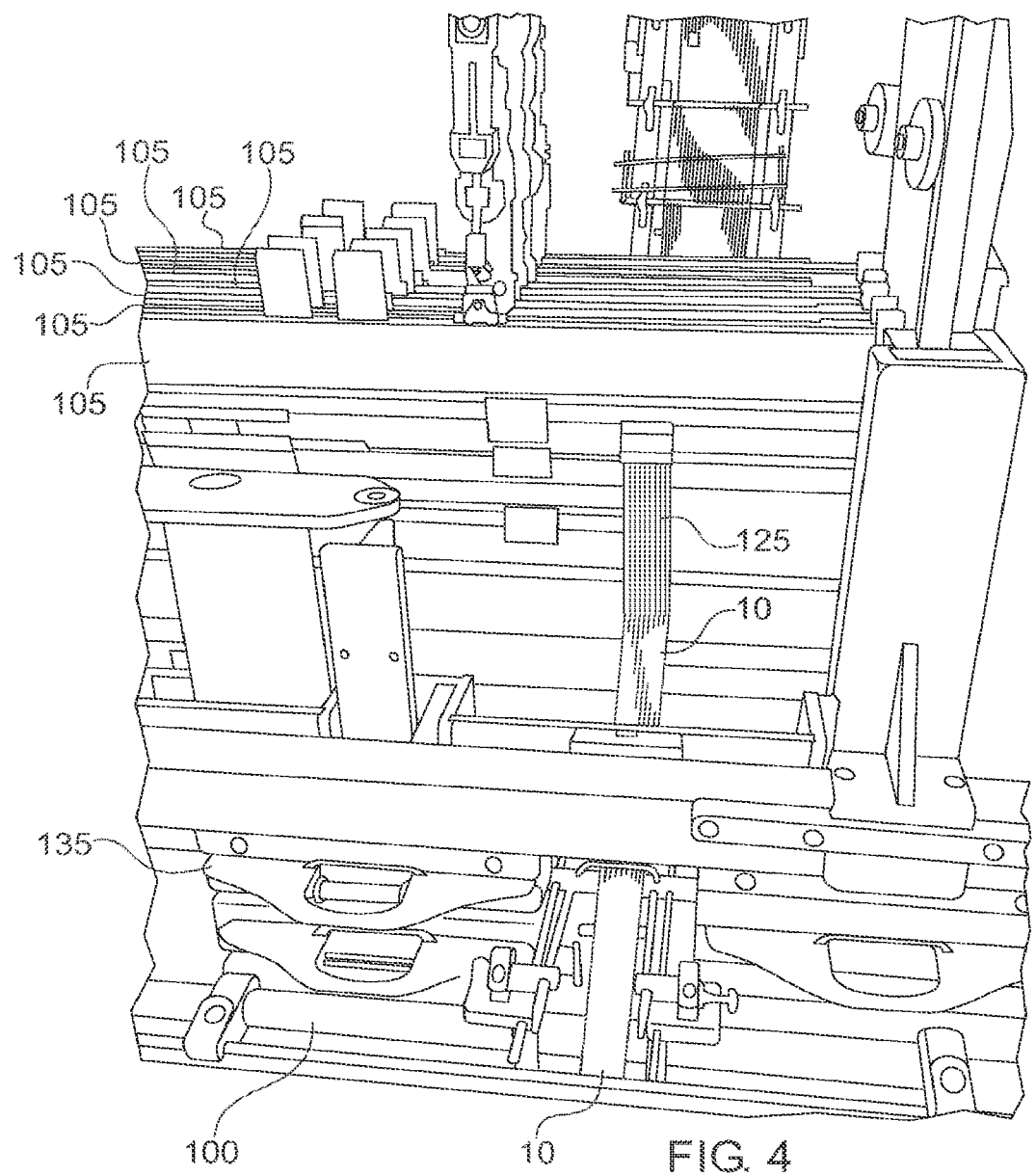
FIG. 4 is a weaving loom for weaving the graft illustrated in FIG. 1.

As shown in FIGS. 1 and 4, the groups of warp yarns dropped during the weaving process are regularly or semi-regularly spaced out across the width of the fabric as the fabric is woven. In this way, each group of dropped yarns may form a ring of yarns circumscribing the graft. The first group of yarns dropped at point 24 in FIG. 1 form the ring of warp yarns designated 67 in FIG. 4. The second group of yarns dropped at point 26 in FIG. 1 form the ring of warp yarns designated 65 in FIG. 4. The third group of yarns dropped at point 28 in FIG. 1 form the ring of warp yarns designated 63 in FIG. 4. As discussed further below, the warp yarns that are dropped during the weaving process are subsequently trimmed. For this reason, in FIGS. 1 and 4 the dropped yarns appear as rings of short fibers protruding from the surface of the graft.

Depending on the trimming process, the ends of the trimmed yarns may be visible as shown in FIG. 4 or the ends may be trimmed so close that the trimmed ends are barely perceptible. Either way, the graft has a generally smooth exterior surface. Furthermore, none of the dropped yarns protrude into the interior of the graft. Accordingly, in the present instance, the surface of the interior wall is substantially constant without surface irregularities along the entire length of the graft, including the tapered section 20.

Figure 2:
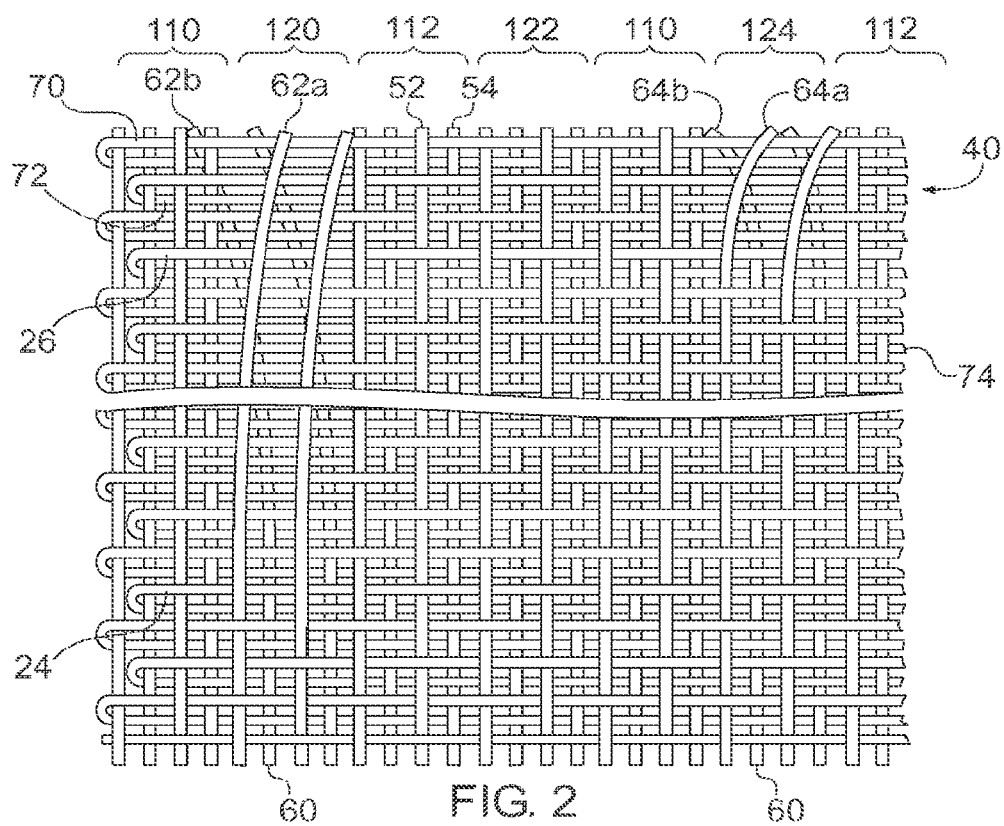
FIG. 2 is an enlarged diagrammatic view of a weave pattern for a portion of the graft illustrated in FIG. 1.
Figure 3:
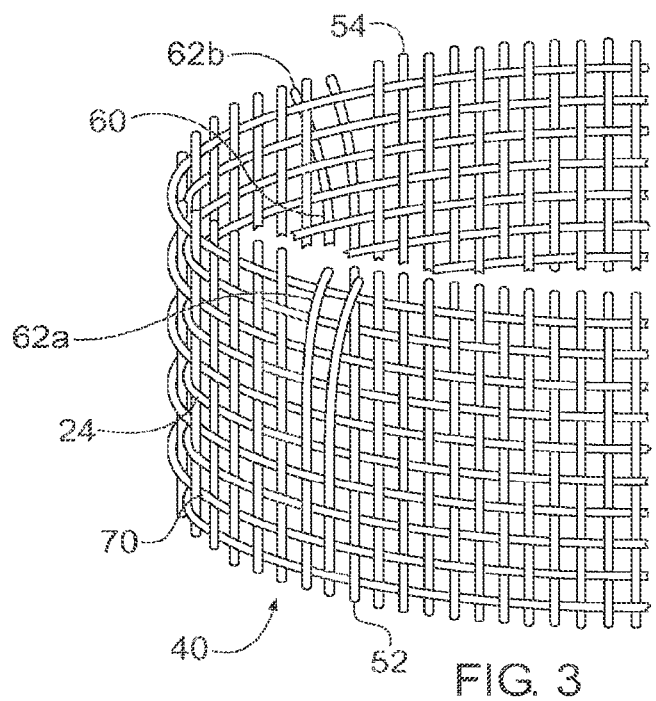
FIG. 3 is an enlarged diagrammatic view of a weave pattern for a portion of the graft illustrated in FIG. 1

Referring to FIGS. 2-3, sections of the fabric of the graft are designated 40. In FIG. 2, a section of fabric is shown in the flat woven form, as it is formed on the weaving machine. In FIG. 3, a section of the fabric is shown after the material is formed into a cylindrical configuration as discussed further below.

The fabric is a double weave fabric formed of a plurality of warp yarns and weft yarns. The warp yarns of the front face are designated 52 and the warp yarns of the rear face are designated 54 in FIGS. 2-3. The weft yarns of the front face are designated 70 and the weft yarns of the rear face are designated 72. The groups of dropped yarns are designated 60, with the warp yarns dropped from the front face designated 62a and the warp yarns dropped from the rear face designated 62b Method for Producing Referring now to FIGS. 4-6D, the method for producing the graft will be described in greater detail. The graft 10 is woven on a loom 100 configured to produce a plain weave double cloth textile. The loom 100 may be any of a variety of types, including, but not limited to a jacquard loom, a circular loom or a dobby loom. In the present instance, the graft is produced on a dobby loom 100. The loom 100 includes a plurality of harnesses 105 for controlling a plurality of heddles 125 that control the warp yarns. In FIG. 4, the heddles are illustrated as wider than the actual heddles, and a smaller number is illustrated than are used in forming the tapered sleeve described below.

Each harness controls a plurality of heddles 125 between a first position and a second position, such as a raised position and a lowered position. The number of harnesses 105 may vary depending on the size and configuration of the graft. In the present instance, the loom utilizes twenty harnesses 105.

From the harnesses 105, the warp yarns pass through a reed 130 having a plurality of slots or dents 132. The reed 130 may be a straight reed or a tapered reed. In the present instance, the reed 130 is a tapered reed so that the reed tapers from a first width down to a second width that is narrower than the first width. Specifically, the reed 130 is widest at the upper end of the reed and is narrowest at the lower end of the reed. In particular, the dents of the reed are spaced out across the width of the reed so that each dent is substantially the same width. The dents 132 taper from the top of the reed to the bottom of the reed so that the dents are widest at the top of the reed and narrowest at the bottom. Alternatively, the reed may be inverted so that the dents and the reed are widest at the bottom and narrowest at the top.

The position of the reed is controlled by a controller that is operable to selectively move the reed up or down to vary the width of the woven fabric. Specifically, moving the reed 130 upwardly pulls or squeezes the warp yarns inwardly, increasing the ends per inch of the fabric if the number of warp yarns remains constant. Similarly, moving the reed downwardly pulls the warp yarns outwardly decreasing the number of ends per inch of the fabric if the number of warp yarns remains constant. The controller may control the timing and rate of reed movement depending on a number of variables, including, but not limited to: the configuration of the graft, the desired density and the number and timing of dropped warp yarns.

The loom 100 also comprises one or more shuttles 135 for weaving the weft yarns 70, 72 onto the warp yarns 52, 54. When a single lumen graft is formed, such as the graft 10 illustrated in FIG. 1, a single shuttle 135 may be used. When a multiple lumen graft is formed, such as the graft 210 illustrated in FIG. 9, multiple shuttles may be used as discussed further below.

Each pass of the shuttle 135 across the warp yarns comprises a pick. When weaving a double cloth textile to form a tubular structure, a pass of the shuttle back and forth completes two pick lines which form a single continuous thread circumscribing the circumference of the tubular fabric. As the shuttle moves forward (left to right from the perspective of FIGS. 2-3), it weaves a pick line on the front face of the fabric. As the shuttle returns (right to left from the perspective of FIGS. 2-3), it weaves a pick line on the rear face of the fabric. By raising and lowering the warp yarns after each forward pass and return pass of the shuttle, the weft yarn from the shuttle continuously weaves from the front face to the rear face without a break or seam.

After the shuttle 135 weaves the weft yarn, the loom moves the reed 130 toward the fell to beat the fabric. The leading edge of the woven fabric is attached to a take-up roll so that the fabric is continuously wound onto the take-up roll as the fabric is finished. The take-up roll also maintains tension on the warp yarns so that the warp yarns are under appropriate tension to weave the fabric. For instance, the take-up roll may be rotated regularly as the weaving process continues. As the take-up roll rotates, the woven material is wound onto the take-up roll, thereby applying tension to the warp yarns.

As discussed above, to weave the fabric, a controller controls the operation of the harnesses 105, the reed 130 and the shuttle(s) to weave the fabric that forms the graft 10. For instance, in order to form a double cloth weave with a tapered section, the yarns are drawn so that a plurality of base warp yarns extend through a plurality of harnesses. Base yarns are yarns that are woven with the weft yarns along the entire length of the graft. At the same time, a plurality of dropped yarns are drawn through a plurality of harnesses. The dropped yarns are woven with the weft yarns for a portion of the graft and are dropped from the woven fabric for a portion of the length of the graft.

For instance, referring to FIG. 1, the first section 12 of the graft is woven by controlling the harnesses through which the base yarns and dropped yarns are drawn so that the weft yarns are woven among all or substantially all the base and dropped yarns. The tapered section 20 is woven by controlling the base yarns and dropped yarns so that the weft yarns are woven among the base yarns, but not all of the dropped yarns. The pattern for dropping the yarns from the weave may vary depending on the configuration of the taper and the desired characteristics of the woven fabric. In particular, the position of the dropped yarns may be controlled so that the dropped yarns are all removed from the weave at substantially the same time. Alternatively, the dropped yarns may be removed gradually.

For example, the dropped yarns may be removed in groups. The total number of dropped yarns may be divided into two or more groups of dropped yarns. At a certain point along the length of the woven fabric, a first group of dropped yarns may be controlled so that the first group of dropped yarns is not woven with the weft yarn. For example, referring to FIG. 1, the first group of dropped yarns may be dropped from the weave at point 24, the second group may be dropped at point 26 and the third group may be dropped at point 28. This progression of dropped yarns is shown in FIGS. 6A-6D.

Figure 6A:
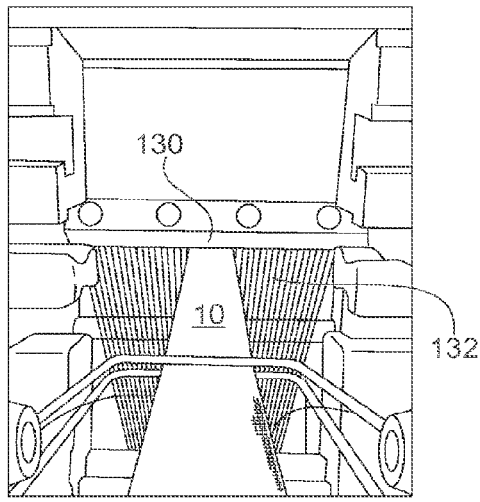
FIGS. 6A-6D is series of views of the graft of FIG. 1 illustrated on the loom of FIG. 4 as the tapered portion of the graft is woven.
Figure 6B:
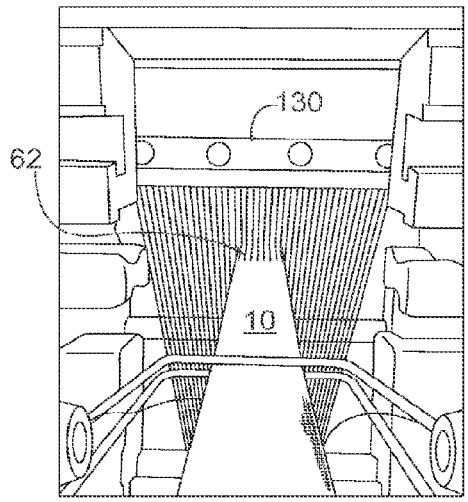
Figure 6C:
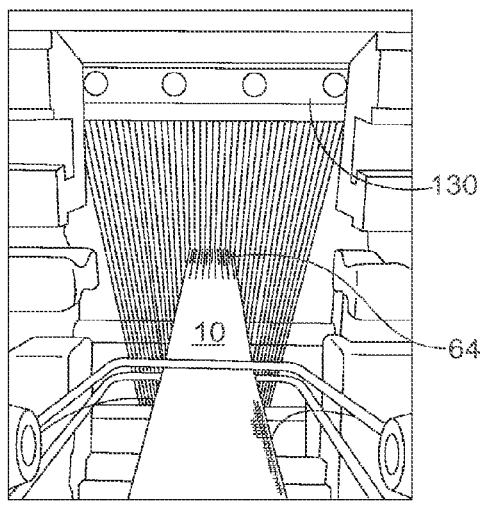

Referring to FIGS. 6A-D, the dropped yarns are spaced apart and extend across the width of the fabric on both the front face (the face shown in FIGS. 6A-D) and the back face (the opposite face that is not visible in FIGS. 6A-D). In FIG. 6A, the fabric 10 is illustrated prior to any yarns being dropped. FIG. 6B illustrated the fabric after a first group of yarns is dropped. FIG. 6C illustrates the fabric after a second group of yarns is dropped, so that both the first and second groups of dropped yarns are visible on the top surface of the fabric 10. Specifically, the first and second groups of dropped yarns are positioned so that the first and second groups of dropped yarns are not woven with the weft yarn as the shuttle 135 moves across the fabric. The process of dropping groups of yarns may repeat until all of the dropped yarns are dropped from the weaving pattern. For example, the third and final group of dropped yarns may be dropped from the weave at point 28 in FIG. 1. The third group of dropped yarns can be seen in FIG. 6D, along with the first and second group of yarns that were dropped earlier in the process.

After all of the dropped yarns are dropped from the weaving pattern, the weaving may continue weaving the base yarns. The result is a flat woven tubular textile having three sections: (1) a first section 12 in which the base and dropped yarns are woven in the fabric; (2) a second section 20 in which the dropped yarns are dropped from the weave; and (3) a third section 16 in which the base yarns are woven without the dropped yarns. In this way, the dropped yarns are interlaced with the weft yarns in the first section 12, but are outside of the weave pattern in part of the tapered section 20 and are outside of the weave pattern in all of the third section 16. The result is a plurality of warp yarns that have a portion woven into the fabric and a portion unwoven. The unwoven portions extend outwardly from the surface of the fabric as shown in FIGS. 2-3, 6B-6D and 9.

As the tapered section 20 is woven, the reed may also be controlled to provide a substantially uniform taper. For instance, referring to FIGS. 1 and 6A-6D, the reed 135 may be moved as the weaving process of the tapered section 20 progresses. While the first portion 12 is being woven, the reed 130 may be lowered so that the reed and the dents 132 are at their widest point for the weave, as shown in FIG. 6A. As the weave process progress, the reed 130 may be raised in a number of steps or it may be raised in a continuous manner depending on the shape of the graft.

Figure 6D:
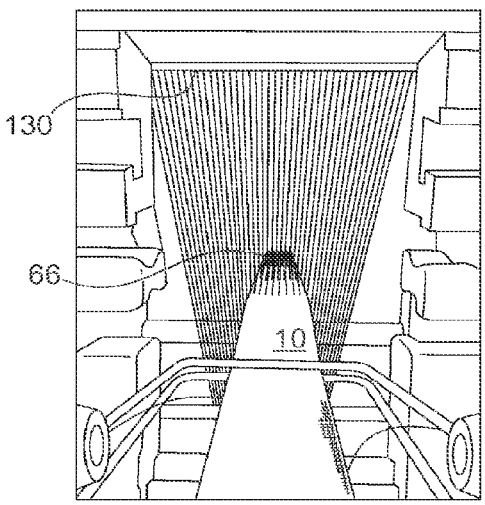

In the present instance, the reed 130 is maintained in the lowered position shown in FIG. 6A while the first section 12 of the graft is woven. At transition point 22 shown in FIG. 1, the reed 130 begins being raised to narrow the width of the fabric. While the tapered section 20 is being woven, the reed 130 is progressively raised as shown in FIGS. 6B-6D. The controller may control the position of the reed so that it is raised at a uniform rate from the lowered position to the raised position. Alternatively, the controller may control the position of the reed so that the movement of the reed accelerates and decelerates as the groups of warp yarns are dropped. In the present instance, the controller controls the position of the reed 130 so that the reed is raised at a generally uniform rate. For example, the reed may be incrementally raised a set amount each time a pick is completed. However, in the present instance the reed is raised an incremental amount each time a predetermined number of picks are completed. The predetermined number of completed picks between movements of the reed may be varied, but preferably the predetermined number is between 5 and 20 picks, and in the present instance the predetermined number is 10 picks. Once the reed is raised to the raised position shown in FIG. 6D, the width of the reed and the dents 132 through which the yarns pass are the narrowest part used during weaving of the graft. The controller then maintains the reed at the raised position shown in FIG. 6D during the weaving of the narrow section 16 shown in FIG. 1.

In the above description the reed 130 is maintained at a generally uniform height while the first section 12 is woven and then moved to a second height and maintained at the second height while the third section 16 is woven. It should be understood that the reed may be moved during the weaving of either the first section or the third section. However, if the reed is moved during weaving of the first or third sections, preferably the reed is moved at a different rate than the rate the reed is moved during weaving of the tapered section 20.

The process of forming the grafts is a continuous weaving process that winds the completed grafts onto a take-up roll. As the weaving of a graft is completed, the dropped yarns are added back into the weaving pattern to widen the width of the woven fabric back out to the widest section of the graft. For instance, referring to FIG. 1, at the end of the weaving process, the woven section of the fabric is as narrow as the width of the third section 16. Warp yarns are added back into the weaving pattern so that the woven fabric is as wide as the first section 12 of the graft.

The dropped yarns may be added back into the weave in a similar manner to how the yarns are dropped from the weave as described above. In other words, the process for adding the dropped yarns back into the weave may proceed by reversing the process used to drop the dropped yarns. Additionally, while the dropped yarns are added back into the weave, the controller controls the reed by lowering the reed to increase the width of the dents through which the warp yarns are drawn. In other words, the dropped yarns and the reed may be controlled so that a graft is woven in reverse of the process described above. In this way, the weaving process forms a graft tapering from wide to narrow and then from narrow to wide. This process repeats for the length of the warp yarns to produce a series grafts in which the weaving alternates between weaving the wide portion first and dropping yarns to weaving the narrow portion first and adding yarns.

Although the grafts may be woven by reversing the weaving process, in the present instance, the grafts are all woven by weaving the wide section first as described above. After a graft is completed, the dropped yarns are added back into the fabric during a transition portion. As the transition portion is woven, the reed 130 is lowered back into the lowered position shown in FIG. 6A. The reed 130 is lowered at a faster rate than when the reed is raised during the weaving of the tapered section. Additionally, the number of picks between adding groups of dropped yarns back into the weave may be less than number of picks between dropping groups of yarns when the tapered section 20 is woven.

After the yarns are added back in so that the fabric is as wide as the first section 12, the weave may not be optimally uniform to provide the uniformly smooth wall surface that is desired for the graft. However, by continuing to weave the fabric at a generally uniform width after the yarns are added back in, the weaving process generally settles into a uniformly woven fabric that provides the uniformly smooth wall surface desired for the graft. Accordingly, between the end of a first graft and the beginning of the next graft, the transition section extends further than the length of the woven section in which the yarns are added back into the web.

Figure 5:
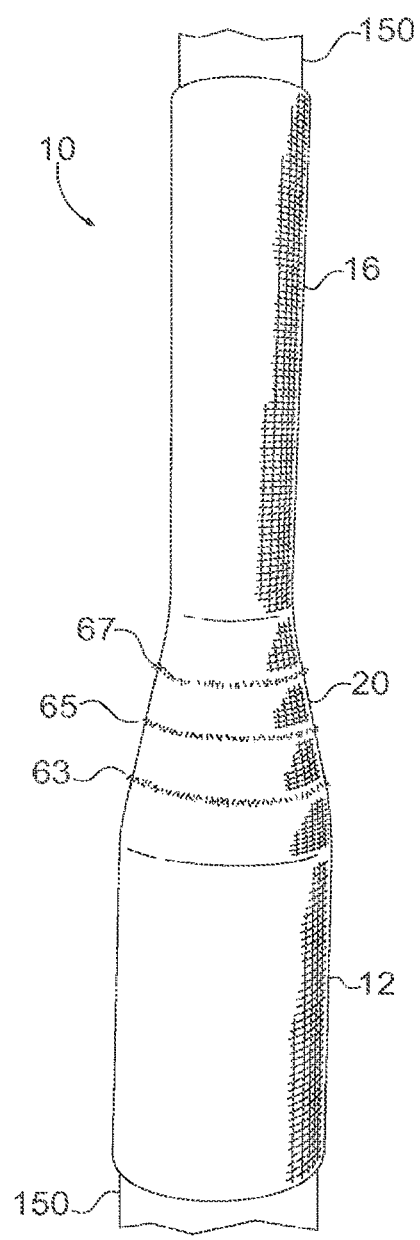
FIG. 5 is a side view of the graft of FIG. 1 illustrated on a mandrel for heat forming the graft.

After weaving, the grafts are trimmed and heat set. Specifically, the graft is cut from the length of fabric that is wound on the take-up roll. The graft is trimmed to length and the tapered transition is cut-off. The result is a flattened double cloth structure with a plurality of loose warp threads protruding from the exterior wall of the fabric. The loose ends are trimmed to minimize the length of thread protruding from the graft. The graft is also heat set to give the graft a generally cylindrical shape. Specifically, as shown in FIG. 5, the graft may be mounted on a mandrel 150 having the desired shape of the graft. In the present instance, the mandrel is a generally cylindrical rod having a first diameter slightly smaller than the internal diameter of the first section. The mandrel also has a frustoconical section that tapers from the first diameter to a narrower diameter similar to the internal taper of the tapered section 20. The mandrel also has a generally cylindrical portion having a diameter slightly smaller than the internal diameter of the second portion 16 of the graft 10. While mounted on the mandrel, the graft is heated above a transition temperature to set the fibers of the graft. Additionally, the fabric may be formed of a material that shrinks when it is heated. In this way, as the graft is heated it shrinks to form a relatively tight fit on the mandrel so that the mandrel molds the graft into the desired shape. For example, in the present instance, the sleeve of woven fabric is slipped over a stainless steel mandrel and heated to approximately 205° F. for 15 minutes. The dropped yarns are then trimmed while the graft is mounted on the mandrel. The finished graft has a generally tubular shape such that the cross-section of the graft is generally circular.

The process for drawing the warp yarns and controlling the position of the warp yarns 52, 54 may vary depending on the configuration of the graft. However, in the present instance, the dropped yarns 60 are interspersed among the warp yarns across the width of the fabric. The dropped yarns are then dropped from the weave in groups. As a result, the woven fabric comprises a ring of dropped yarns spaced apart around the circumference of the graft. Specifically, referring to FIG. 1, at point 24 a ring is formed of a plurality of fibers that protrude from the outer surface of the woven fabric. The protruding fibers are generally equally spaced apart around the circumference of the woven fabric. At point 26 a second ring is formed where the second group of fibers was dropped and at point 28 a third ring is formed where the third group of fibers was dropped.

EXAMPLE 1

Figure 7A:
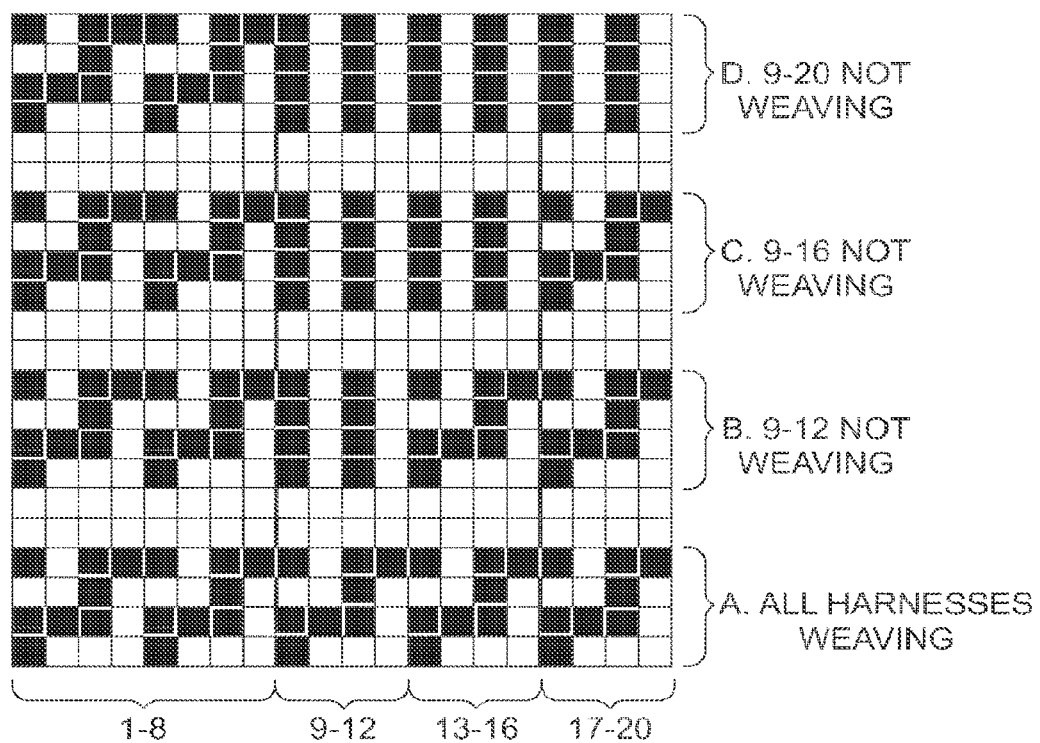
FIG. 7A is a diagram of the design set-up for weaving the graft of FIG. 1.
Figure 7B:
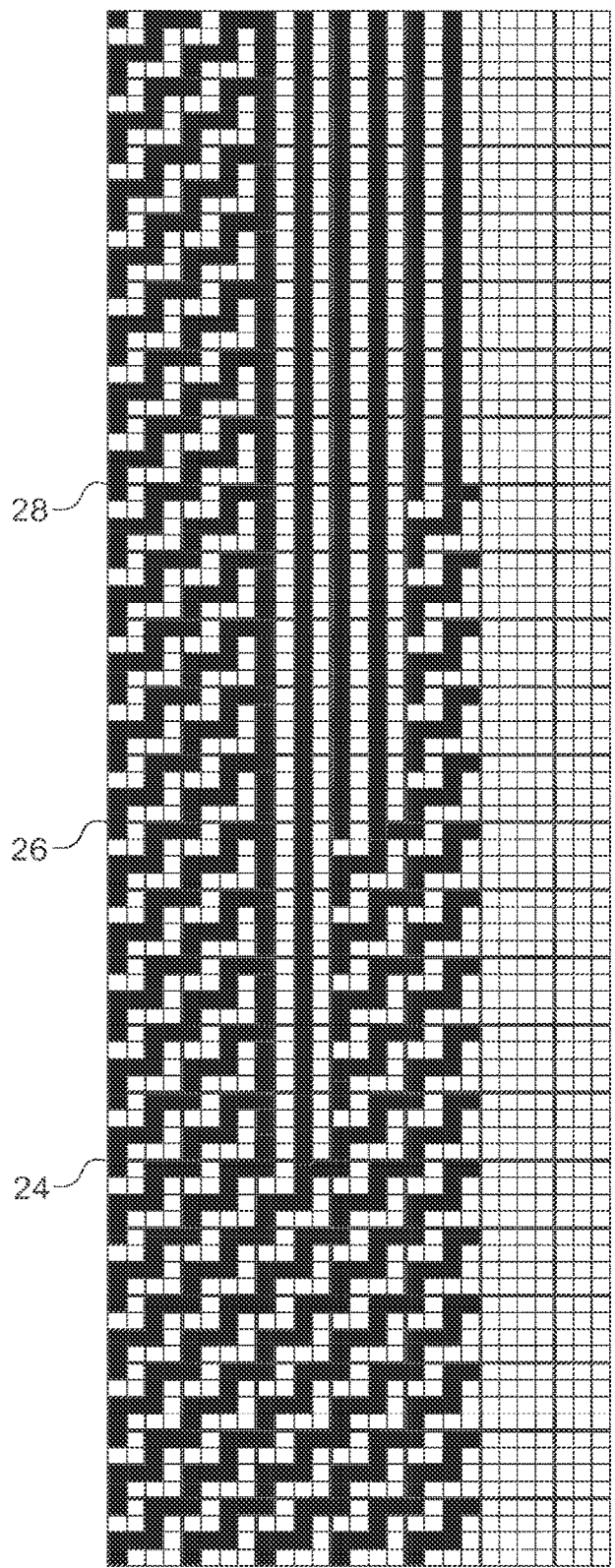
FIG. 7B is a diagram of the design set-up for weaving the graft of FIG. 1.
Figure 8:
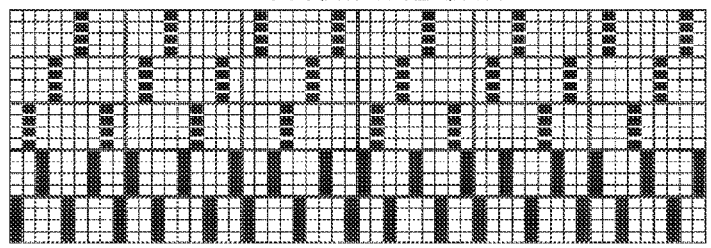
FIG. 8 is a diagram of the harness draw for weaving the graft of FIG. 1.

Referring now to FIGS. 7A, 7B and 8, an exemplary weaving process is described for forming a tubular graft such as the graft illustrated in FIGS. 1, 2 and 4. The graft is a 28 mm×16 mm graft in which the first section 12 is substantially cylindrical having a 28 mm diameter and the second section 16 is substantially cylindrical having a 16 mm diameter. The tapered section 20 tapers at a substantially uniform rate from the first section 12 to the second section 16.

The fabric comprised 900 warps yarns including 500 primary yarns that were woven throughout the length of the graft and 400 supplementary yarns that were woven in the first section 12 and then gradually dropped in the tapered section 20. The 400 supplementary yarns were not woven into the second section 16.

The primary yarns were spooled on a first warp beam and the supplementary yarns were spooled on a second warp beam. The 900 warp yarns were drawn through twenty harnesses using a straight draw. The 500 primary yarns were drawn through harnesses 1-8 and the 400 supplementary yarns were drawn through harnesses 9-20. During the weaving process, the supplementary yarns were dropped in three different groups. The first group of dropped yarns was drawn through harnesses 9-12. The second group of dropped yarns was drawn through harnesses 13-16 and the third group of dropped yarns was drawn through harnesses 17-20.

FIG. 8 is a diagram illustrating the sequence for the harness draw. The diagram shows the sequence of the yarns across the width of the fabric and which harness controlled which yarns. The diagram is read from left to right, starting in the bottom left-hand corner of FIG. 8. Referring to FIGS. 2 & 8, the first four warp yarns of the fabric were drawn through the first four harnesses, which are designated 110 in FIG. 2. Specifically, the first warp yarn was threaded through the first heddle of the first harness, the second warp yarn was threaded through the first heddle of the second harness, the third warp yarn was threaded through the first heddle of the third harness and the fourth warp yarn was threaded through the first heddle of the fourth harness. As mentioned above, the warp yarns of the front face of the double cloth fabric are designated 52 in FIG. 2. The warp yarns of the back face are designated 54.

The following table details the sequence of drawing a section of yarns through the heddle of the harnesses in a manner similar to that described above:

| Ref No. (in FIG. 2) | Yarn Nos. | Yarn Type | Harnesses |
|---|---|---|---|
| 110 | 1-4 | Base | 1-4 ($1^{st}$ heddle) |
| 120 | 5-8 | Supplementary | 9-12 ($1^{st}$ heddle) |

-continued

| Ref No. (in FIG. 2) | Yarn Nos. | Yarn Type | Harnesses |
|---|---|---|---|
| 112 | 9-12 | Base | 5-8 ($1^{st}$ heddle) |
| 122 | 13-16 | Supplementary | 13-16 ($1^{st}$ heddle) |
| 110 | 17-20 | Base | 1-4 ($2^{nd}$ heddle) |
| 124 | 21-24 | Supplementary | 17-20 ($1^{st}$ heddle) |
| 112 | 25-28 | Base | 5-8 ($2^{nd}$ heddle |

The sequence of yarns continued in this fashion according to the diagram in FIG. 8. Once the draw sequence reached the right-hand edge of the diagram in FIG. 8, the sequence repeated beginning in the bottom left-hand corner of the diagram (i.e. harnesses 1-4). The sequence of drawing yarns continued until all 900 yarns were drawn through the twenty harnesses. As can be seen, the number of yarns drawn through each harness was different. For instance, the number of yarns drawn through each of harnesses 1-8 (the base yarns) was different than the number of yarns drawn through each of harnesses 9-20.

FIGS. 7A and 7B are diagrams that illustrate how the harnesses were controlled during the weaving process. FIG. 7A provides enlarged views of portions of the diagram illustrated in FIG. 7B. The diagram is read starting from the left-hand side at the lower edge. A black mark indicates that the harness was raised. No mark indicates that the harness was not raised so that the harness was in a lowered position.

Starting at the bottom left, the sequence for the harness control was as follows. For the first pick line, the $1^{st}$, $5^{th}$, $9^{th}$, $13^{th}$ and $17^{th}$ harnesses were raised. The remaining harnesses remained lowered. The shuttle 125 then passed across the width of the fabric through the shed formed between the raised and lowered harnesses. Harnesses 1-3, 5-7, 9-11, 13-15 and 17-19 were then raised while harnesses 4, 8, 12, 16 and 20 were lowered. The shuttle then passed across the width of the fabric. In line three, harnesses 4, 8, 12, 16 and 20 were raised while the rest of the harnesses were lowered and the shuttle then passed across the width of the fabric. In line four, harnesses 2, 6, 10, 14 and 18 were lowered while the remaining harnesses were raised. The shuttle then passed across the width of the fabric. The series of these first four lines was repeated to form the first section 12 of the graft shown in FIG. 1.

While the first portion 12 of the graft 10 was woven, the reed 130 remained in the lowered position as shown in FIG. 6A. After the first portion 12 of the graft was completed, the reed 130 was raised at a uniform rate along the length of the tapered section 20. Specifically, the reed was raised approximately 0.75 mm every 5 picks. In this way, transverse forces were applied to the warp yarns to narrow the width of the fabric. Specifically, the fabric was compressed across its width during the weaving process to reduce the width of the fabric.

During weaving of the tapered section 20, the supplemental yarns 60 were dropped in three groups. The first group of supplemental yarns 60 were dropped at the point designated 24 in FIGS. 1, 2 and 7B. The yarns were dropped by raising harnesses 9 and 11, lowering harnesses 10 and 12 and holding harnesses 9-12 in the respective raised and lower positions while the remaining harnesses were raised and lowered according to the pattern in FIGS. 7A and 7B. As shown in FIG. 7B, twenty picks after the first group of yarns were dropped, the second group of yarns were dropped at the point designated 26 in FIGS. 1, 2 and 7B. The second group of yarns was dropped by raising harnesses 13 and 15 and lowering harnesses 14 and 16 so that harnesses 9-16 were held in their respective raised and lowered positions while harnesses 1-8 and 17-20 were raised and lowered according to the pattern shown in FIGS. 7A and 7B. Twenty picks after the second group of yarns were dropped, the third group of yarns was dropped at the point designated 28 in FIGS. 1, 2 and 7B. The third group of yarns were dropped by raising harnesses 17 and 19 and lowering harnesses 18 and 20 so that harnesses 9-20 were held in their respective raised and lowered positions while harnesses 1-8 were raised and lowered according to the pattern shown in FIGS. 7A and 7B.

FIG. 2 illustrates a section of fabric 40 woven according to the process described above in Example 1. However, for illustrative purposes, the fabric is shown at a constant width, as if the reed 130 was not raised during the weaving process in which the yarns were dropped.

In FIG. 2, the front face was woven from warp yarns 52 and pick yarns 72. The back face was woven from warp yarns 54 and pick yarns 70. The first group of dropped yarns 60 was dropped after the pick yarn at 24. The second group of dropped yarns 60 was dropped after the pick yarn at 26. The loose ends of the yarns dropped from the front face are designated 62a, 64a. The loose ends of the yarns dropped from the rear face are designated 62b, 64b.

Since the loose ends of the dropped yarns 60 were not woven with the pick yarns, the loose ends overlie the pick yarns in the fabric because the harnesses for the dropped yarns of the front face remained in the raised position and the harnesses for the dropped yarns of the back face remained in the lowered position as shown in FIG. 7B. In this way, all of the loose ends protrude from the outside of the woven tube. Alternatively, the loose ends may extend into the inside of the woven tube by reversing the drop pattern by altering the sequence of controlling the raising and lowering of the warp yarns.

FIG. 2 is only a fragment of the overall width of the fabric 40. The fragment shows twenty-six of the nine hundred warp yarns that formed the graft. The yarn sequence for the rest of the fabric followed the pattern set forth in FIGS. 7A and 7B. As shown in FIGS. 2-3, the result was a fabric having a plurality of yarns dropped from both faces of the fabric with the dropped yarns being spaced out across the width of both sides of the fabric. Therefore, the dropped yarns were spaced out around the circumference of the graft. The dropped yarns are bounded on either side by warp yarns that remain in the woven fabric. Transverse forces applied along the direction of the pick yarns during the beating process reduce the distance between adjacent warp yarns in the woven fabric after the warp yarns were dropped.

EXAMPLE 2

Figure 9:
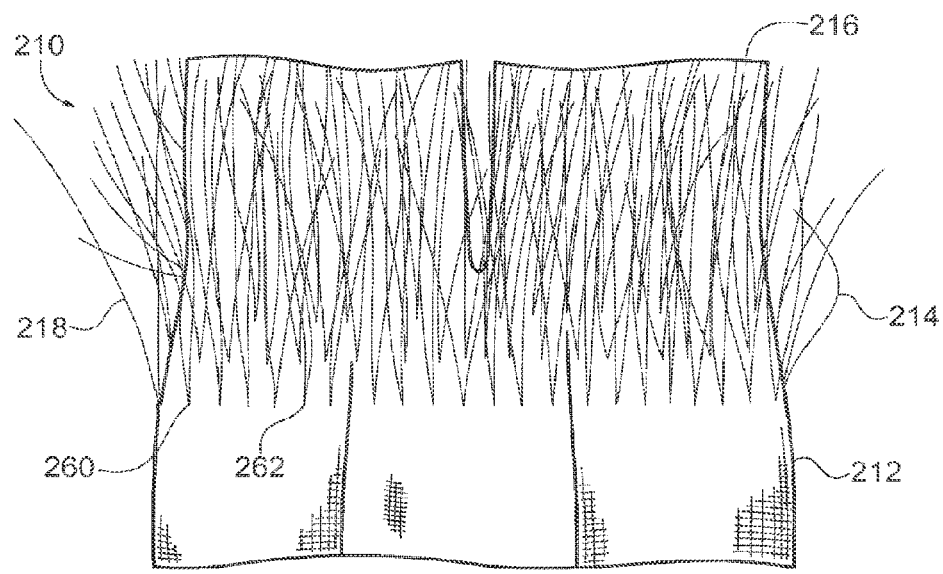
FIG. 9 is a side view of a bifurcated tapered tubular graft.

Referring now to FIG. 9, a second graft is designated generally 210. The graft 210 is a bifurcated graft having a body 212 that bifurcates to form two branches 216, 218. The body 212 is generally cylindrical and tapers at tapered section 214 from a first diameter to a smaller second diameter. From the reduced diameter end, the graft branches into the first and second branches 216, 218.

As can be seen in FIG. 9, during weaving of the tapered section 214 a plurality of the warp yarns are dropped around the graft so that the dropped yarns protrude from the surface of the graft. As in the previously described graft 10, the dropped yarns of the bifurcated graft 210 are spaced apart around the circumference of the graft.

The bifurcated graft 210 can be utilized in a variety of applications. For instance, the bifurcated graft was formed as a woven stent graft. The body 212 is a 36 mm aortic portion and the two branches 216, 218 form two 14 mm iliacs. The graft 210 is woven with 1/40/27/12Z PET filament in a plain weave construction. The aortic region 212 is a double-cloth tube that tapers to the two narrower double-cloth tubes. The aortic section has 1122 warp yarns, a plurality of which are dropped from the weave pattern when weaving the tapered section 214. In particular, the warp yarns were controlled so that ninety-four warp yarns were dropped three times during the weaving of the tapered section. Fifty picks after the first group of yarns was dropped, the second group of yarns was dropped. Fifty picks after the second group of yarns was dropped, the third group of yarns was dropped.

During weaving of the tapered section 214, the fabric was also narrowed by raising a tapered reed through which the warp yarns were drawn. The reed was raised to taper the fabric 0.767 mm narrower every 10 picks of the tapered section weave. The dropped yarns were dropped evenly in pairs around the circumference of the tapered section 212. As a result of dropping the warp yarns, the two branches 216, 218 were woven with 420 warp yarns each. The graft is seamless because the shuttles wove the weft yarns around the tubular graft and each of the branches to form a continuous fabric structure.

As with the first example described above, the bifurcated graft 210 was woven on a dobby shuttle loom using twenty harnesses. Although a dobby loom was used, it should be understood that other looms could be used to control the weaving process as described above. For instance, a jacquard loom could be used to control the weaving pattern.

The loom used three shuttles to weave the fill yarns. The first shuttle wove fill yarns around the entire circumference of the body 212 and the tapered section 214. A second shuttle wove fill yarn around the entire circumference of the first branch 216 and a third shuttle wove fill yarn around the entire circumference of the second branch 218. The warp yarns for the fabric were fed from three beams: a first beam for the warp yarns forming the first branch 216; a second beam for the warp yarns forming the second branch 218; and a third beam for the warp yarns to be dropped during weaving of the tapered section.

As in the first example, harnesses 1-8 were used for warp yarns that were woven through the entire length of the graft. More specifically, harnesses 1, 3, 5 and 7 were used to control the warp yarns that formed the first branch 216. Harnesses 2, 4, 6 and 8 were used to control the warp yarns that formed the second branch 218. Harnesses 9-20 were used to control the warp yarns that were dropped during weaving of the tapered section 214.

The ratio between the total number of warp yarns in the body 212 and the total number of warp yarns in the combination of the two branches 216, 218 was calculated to determine the number of warp yarns drawn versus the number of warp yarns dropped. The calculated value for this ratio was multiplied by four to determine the number of warp yarns in the draw. For instance, if the ratio of total warp yarns used to the number of warp yarns dropped would be 3 to 1 then the number of warp yarns drawn to warp yarns dropped would be 12:4. If the ratio is 4 to 1, the number of warp yarns woven to warp yarns dropped would be 16:4. Similar to the first example, the warp yarns are drawn together with the dropped yarns so that the dropped yarns are interleaved evenly across the face of the fabric in groups of four, where two yarns of each group form the front face and two yarns of each group form the back face of the fabric. The base warp yarns formed the two branches 216, 218. In other words, the base yarns are woven in the fabric along the entire length of the graft.

The bifurcated graft was woven from 1122 warp yarns and 282 warp yarns were dropped when weaving the tapered section 214. Accordingly, using the ratio of 12:4 the following table details the sequence of drawing a section of yarns through the heddles of the harnesses in a manner similar to that described above for Example 1:

| Yarn Nos. | Yarn Type | Harnesses |
| --- | --- | --- |
| 1-4 | Base | 1, 3, 5, 7($1^{st}$ heddle) |
| 5-8 | Base | 1, 3, 5, 7($2^{nd}$ heddle) |
| 9-12 | Base | 1, 3, 5, 7($3^{rd}$ heddle) |
| 13-16 | Supplementary | 9-12 ($1^{st}$ heddle) |
| 17-28 | Base | 1, 3, 5, 7 repeated 3 times using heddles 5-8 |
| 29-32 | Supplementary | 13-16 ($1^{st}$ heddle) |
| 33-44 | Base | 1, 3, 5, 7 repeated 3 times using heddles 9-12 |
| 44-48 | Supplementary | 17-20 ($1^{st}$ heddle) |
| 49-528 | Base/supplemental | Repeat pattern above 10 more times |
| 529-540 | Base | 1, 3, 5, 7 (repeat three times) |
| 541-544 | Supplemental | 9-12 |
| 545-556 | Base | 1, 3, 5, 7 (repeat three times) |
| 557-560 | Supplemental | 13-16 |
| 561-572 | Base | 2, 4, 6, 8 (repeat three times using heddles 1-3) |
| 573-576 | Supplemental | 17-20 ($1^{st}$ heddles) |
| 577-588 | Base | 2, 4, 6, 8 (repeat three times using heddles 4-6) |
| 589-592 | Supplemental | 9-12 |
| 593-604 | Base | 2, 4, 6, 8 (repeat three times using heddles 9-12) |
| 605-608 | Supplemental | 13-16 |
| 609-620 | Base | 2, 4, 6, 8 (repeat 3 times using heddles 13-15) |
| 621-624 | Supplemental | 17-20 |
| 625-1104 | Base/supplemental | Repeat pattern above 10 times for yarns 561-624 |
| 1105-1122 | Base | (2, 4, 6, 8) repeat 4 times |

The tapered reed was maintained at a generally constant position while weaving the body 212 as a substantially cylindrical tube at 150 picks per inch. After pick 1000, the reed was raised every ten picks as the next 200 picks were woven. At pick 1050 the warp yarns from harnesses 9-12 were dropped out of the weave pattern. At pick 1100 the warp yarns from harnesses 13-16 were dropped out of the weave pattern. At pick 1150 the warp yarns from harnesses 17-20 were dropped out of the weave pattern. At pick 1201 the pattern started weaving the first and second branches 216, 218. The shuttle used to weave the weft yarns with the warp yarns for the body 212 was discontinued. Instead, the second shuttle wove weft yarns around the warp yarns of harnesses 1, 3, 5, 7 and the third shuttle wove weft yarns around the warp yarns of harness 2, 4, 6, 8.

Similar to the first example, the warp yarns dropped from the weaving pattern were dropped by raising or lowering the respective warp yarns and maintaining the dropped yarns in a raised or lowered position while continuing to weave the base warp yarns.

At pick 6001 the weaving for the graft is completed and the dropped yarns were incrementally added back into the weaving pattern while the reed was lowered to widen the width of the reed where the warp yarns were drawn through the reed. In the present example, the dropped yarns were added back into the weave pattern twice as fast as the yarns were dropped.

After the graft was woven, the fabric was mounted onto a stainless steel mandrel having the shape of the finished bifurcated graft. The fabric was heated to 205 degrees Fahrenheit for 15 minutes while the fabric was mounted on the mandrel. After heating, the dropped ends protruding from the surface of the fabric were trimmed.

It will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

We claim:

1. An implantable woven graft, comprising:
a first tubular section wherein the first section comprises a fabric woven from a plurality of base yarns and a plurality of supplemental yarns, wherein
the first tubular section has a first diameter and a number of warp yarns per inch;
a frustoconically-shaped hollow tapered section having a first diameter that is substantially the same as the first diameter of the first tubular section and a second diameter, wherein the frustoconically-shaped hollow tapered section comprises a fabric woven from the base yarns forming the first tubular section and a plurality of the supplemental yarns, wherein the plurality of supplemental yarns are dropped from a weave pattern in the frustoconically-shaped hollow tapered section so that ends of the plurality of supplemental yarns protrude from a surface of the frustoconically-shaped hollow tapered section, wherein the protruding supplemental yarns are spaced apart from one another around a circumference of the frustoconically-shaped hollow tapered section,
wherein the plurality of supplemental yarns are dropped along a single pick line so that ends of the protruding supplemental yarns are spaced apart around the circumference along the pick line, and
wherein a number of warp yarns per inch at the second diameter is within 20% of a number of warp yarns per inch at the first diameter.

2. The implantable woven graft of claim 1, wherein a second group of supplemental yarns are dropped from the weave pattern in the frustoconically-shaped hollow tapered section so that ends of the second group of supplemental yarns are spaced apart around the circumference of the frustoconically-shaped hollow tapered section.

3. The implantable woven graft of claim 2, wherein the second group of supplemental yarns are dropped from the weave pattern along a second pick line spaced apart from the pick line at which the plurality of supplemental lines are dropped.

4. The implantable woven graft of claim 1, wherein the protruding ends of the dropped plurality of supplemental yarns form a ring circumscribing the frustoconically-shaped hollow tapered section.

5. The implantable woven graft of claim 1, wherein the number of warp yarns per inch at the second diameter is within 10% of the number of warp yarns per inch at the first diameter.

6. The implantable woven graft of claim 1, wherein the number of warp yarns per inch at the second diameter is within 5% of the number of warp yarns per inch at the first diameter.

7. An implantable woven graft, comprising:
a first tubular section wherein the first section comprises a fabric woven from a plurality of base yarns and a plurality of supplemental yarns, wherein
the first tubular section has a first diameter and a number of warp yarns per inch;
a frustoconically-shaped hollow tapered section having a first diameter that is substantially the same as the first diameter of the first tubular section and a second diameter, wherein the frustoconically-shaped hollow tapered section comprises a fabric woven from the base yarns forming the first tubular section and a plurality of the supplemental yarns, wherein the plurality of supplemental yarns are dropped from a weave pattern in the frustoconically-shaped hollow tapered section so that ends of the plurality of supplemental yarns protrude from a surface of the frustoconically-shaped hollow tapered section, wherein the protruding supplemental yarns are spaced apart from one another around a circumference of the frustoconically-shaped hollow tapered section, and
wherein a number of warp yarns per inch at the second diameter is substantially the same as a number of warp yarns per inch at the first diameter.

8. The implantable woven graft of claim 7, wherein the protruding supplemental yarns spaced apart from one another around the circumference of the frustoconically-shaped hollow tapered section form a ring of yarns having a substantially uniform width circumscribing the graft.

9. The implantable woven graft of claim 7, wherein the plurality of supplemental yarns do not protrude into the interior of the graft.

10. The implantable woven graft of claim 7, wherein the woven fabric includes a double cloth.

\* \* \* \* \*